(12) United States Patent
Dimmick (10) Patent No.: US 7,135,035 B1
(45) Date of Patent: Nov. 14, 2006

(54) THERMODYNAMIC RESONANCE ENCLOSURE

(76) Inventor: Walter F. Dimmick, 1090 Heritage Pl., Auburn, CA (US) 95603

(\*) Notice: Subject to any disclaimer, the term of this patent is extended or adjusted under 35 U.S.C. 154(b) by 343 days.

(21) Appl. No.: 10/446,399

(22) Filed: May 27, 2003

(51) Int. Cl.
*A61N 5/06* (2006.01)
*E04B 7/16* (2006.01)

(52) U.S. Cl. .................... 607/90; 52/67; 52/64; 607/91
(58) Field of Classification Search ............ 52/67, 52/64; 312/129; 607/88–91, 96
See application file for complete search history.

(56) References Cited

U.S. PATENT DOCUMENTS

| | | | |
|---|---|---|---|
| 558,394 A | 4/1896 | Kellogg | |
| 664,081 A | 12/1900 | Gohlin | |
| 828,733 A | 8/1906 | Fuller | |
| 2,420,454 A | 5/1947 | Lind | |
| 2,655,155 A | 10/1953 | Achner | |
| 3,741,218 A | 6/1973 | Novak | |
| 3,832,810 A * | 9/1974 | Johnston | 52/67 |
| 4,132,456 A * | 1/1979 | Lewis et al. | 312/126 |
| 4,309,999 A | 1/1982 | Lueder | |
| 4,582,062 A | 4/1986 | Albini | |
| 4,773,105 A * | 9/1988 | Toyoshima | 4/526 |
| 6,745,411 B1 * | 6/2004 | Kjonaas | 4/524 |

OTHER PUBLICATIONS

Dimmick, Walter F.; Pyramid Science and Unified Field; 1996; Gilroy, California.

\* cited by examiner

*Primary Examiner*—Roy D. Gibson
(74) *Attorney, Agent, or Firm*—Heisler & Associates

(57) ABSTRACT

An enclosure is provided generally in the form of a box which provides a controlled thermal environment for the occupant. The enclosure includes a horizontal base supporting four corner posts extending vertically up from the base, with a roof above the posts and parallel with the base. A rear wall extends in a vertical plane from the base up to the roof. A pair of side walls extend from the base up to the roof. The side walls preferably include surfaces to maximize maintenance of heat within the enclosure particularly near a position for an occupant's head. Thermal sources (i.e. incandescent light bulbs) are located within the enclosure to increase an amount of infrared radiation for heating within the enclosure. A width tuning system is provided to precisely position a distance of the side walls away from each other so that thermodynamic resonance between the side walls can be maximized.

6 Claims, 3 Drawing Sheets

THERMODYNAMIC RESONANCE ENCLOSURE

FIELD OF THE INVENTION

The following invention relates to enclosures for maintaining a controlled thermal controlled environment therein, such as to provide a comfortable environment for human occupation while conserving energy necessary to maintain a desirable temperature within the enclosure. More particularly, this invention relates to enclosures which are sized, shaped and otherwise outfitted to utilize thermodynamic resonance to efficiently maintain a comfortable environment for human occupancy therein.

BACKGROUND OF THE INVENTION

Significant natural resources are spent in maintaining comfortable thermal environments for human occupancy, particularly in low temperature climates. The delivery of these natural resources to residences in the form of hydrocarbon gases, heating oil or electricity, largely generated from combustion of such hydrocarbon fuels, involves considerable expense for the occupants of the residence. Much of this energy is expended to maintain a comfortable temperature within the residence when the occupants are residing therein. These times are typically in the early evening and night when temperatures tend to lower.

Occupants of residential structures typically spend a significant amount of evening and nighttime in a largely motionless state involved in activities such as eating, watching television, reading a book, working with a computer, or sleeping. The occupant only utilizes a small amount of space during these activities. However, the entire residence, or significant portions thereof, are typically heated during this time period, resulting in significant heat waste. Accordingly, it is logical and desirable that only the particular spaces occupied by the resident be heated, rather than the entire interior of the residence.

Enclosures are known in the art for maintaining a small region at a high temperature. However, such enclosures are typically provided not to expose the occupant to minimal heat to provide comfort, but to achieve a therapeutic benefit. Sauna rooms provide one such example. Also, the patents to Kellogg (U.S. Pat. No. 558,394), Gohlin (U.S. Pat. No. 664,081), Fuller (U.S. Pat. No. 828,733), Lind (U.S. Pat. No. 2,420,254), Achner (U.S. Pat. No. 2,655,155), Novak (U.S. Pat. No. 3,741,218), Lueder (U.S. Pat. No. 4,309,999) and Albini (U.S. Pat. No. 4,582,062) provide various different enclosures with heat sources therein, typically light bulbs, to deliver high levels of heat and infrared radiation to the occupant.

Such prior art enclosures suffer from requiring very large amounts of electric or other energy to operate according to their designs. Also, they provide significantly greater levels of heat than that required to merely efficiently maintain a comfortable environment within the enclosure.

The basic principles of heat transfer establish what temperatures will be achieved within a particular environment based on the size of the environment, the amount of heat energy being directed into the environment, and the heat transfer characteristics of the materials forming the enclosure surrounding the environment. Specifically, heat transfer occurs according to one of three modes including radiation heat transfer, convection heat transfer and conduction heat transfer. By properly evaluating the quantity of each of these forms of heat transfer relative to a controlled thermal environment, the temperature within that environment can be calculated.

Additionally, some forms of heat transfer have a greater impact on the comfort level and temperature perceived by a human occupant, than other forms of heat transfer. Specifically, it has been well established that a room with a temperature of 70° F. but with cold walls perhaps below freezing (a typical situation in northern latitudes of North America in winter) will feel rather chilly, due to the radiation heat transfer out of the occupants of the room and into the cooler walls of the room. The occupants will not be comfortable in short sleeves in such an environment, but rather will typically wear long sleeved shirts, long pants, and perhaps a sweater to maintain comfort.

In contrast, the same room with a 70° F. air temperature but with warmer walls (such as during a hot summer day with an exterior temperature of perhaps 90° F. or more), will provide a rather warm perception for the occupants of the room. Radiation heat transfer from the warm walls of the room into the occupants will cause the occupants to typically prefer short sleeve shirts and perhaps short pants to maintain comfort within such a room.

Similarly, the degree to which the air is flowing against the occupants within the thermally controlled space will have an effect on the perceived temperature of the room, even though the actual temperature of air within the room might be different than that perceived by the occupant. Accordingly, it is desirable that an enclosure configured to maintain a comfortable space within the enclosure and maintaining a low cost to operate would maximize the perception of temperature within the enclosure while minimizing the actual air temperature within the enclosure for highest efficiency. Such a maximization can particularly be provided by maximizing the perceived radiation heat transfer into the occupant from walls of the enclosure in as energy efficient a manner as possible. The enclosure also beneficially minimizes air flow by natural convection or other convection forces so that the somewhat chilling effect of cool air flowing over the occupant is avoided.

To maximize the apparent temperature of the occupant due to radiation heat transfer into the occupant, it is beneficial to additionally take advantage of the concept of thermodynamic resonance. Thermodynamic resonance is described in detail in the book entitled "Pyramid Science and the Unified Field, Second Edition" by Walter F. Dimmick, copyright 1996. This concept of thermodynamic resonance is based on the observation that electromagnetic radiation, including infrared wave lengths of electromagnetic radiation responsible for radiation heat transfer, resonate at particular distances in a manner analogous to that of a standing wave, so that at specific distances away from a radiant heat source a greater perceived level of radiation heat transfer is experienced, particularly by a human occupant. In particular, distances which fall into increments of half hydrogen cubits identify points where peaks occur in such standing waves and a maximum amount of perceived radiation heat transfer is experienced. A hydrogen cubit is defined as 25.025 inches, or 25 hydrogen inches, where each hydrogen inch is 1.001 standard or American inches.

Correspondingly, odd increments of quarter hydrogen cubits exactly halfway between the increments of half hydrogen cubits define locations in such thermodynamic resonance standing waves where a particularly low amount of radiation heat transfer is perceived, particularly by a human observer. Accordingly, a need exists for an enclosure which is sized, shaped and configured to maximize utilization of concepts of radiation heat transfer and thermodynamic resonance so that a warmest possible perceived interior controlled thermal environment can be maintained within the enclosure while an actual physically measured air temperature within the enclosure is as low as possible. In this way, a minimum amount of resources and associated cost is expended to maintain such a desirable perceived controlled thermal environment within the enclosure.

SUMMARY OF THE INVENTION

This invention provides an enclosure which efficiently and economically provides a comfortable thermal environment therein for human occupancy. Particularly, the enclosure includes side walls which are spaced apart a distance which is an increment of half hydrogen cubits from each other. Between the side walls a radiant heat source, such as an incandescent light bulb (or multiple such light bulbs) can be provided between the side walls to provide a source of radiant heat. Infrared radiation resonates between reflective surfaces of the side walls to maximize a perceived temperature within the enclosure. The enclosure beneficially additionally includes a rear wall and a roof, and optionally a door so that convection heat transfer can be inhibited between the controlled thermal environment within the enclosure and other portions of the room within which the enclosure is located. The various different walls of the enclosure are preferably insulated to inhibit conduction heat transfer through the walls thereof so that a comfortable temperature can be maintained within the enclosure with a minimal temperature outside the enclosure.

Preferably, the side walls are configured to be tunable to have a precise distance therebetween adjusted so that thermodynamic resonance between the side walls can be maximized. Most preferably, this tuning system is in the form of a tuning bar extending between corner posts adjacent front and rear edges of the side walls. At least one adjustable length fastener extends between each tuning bar and the adjacent side wall. By adjusting the length of this fastener, the side walls can be brought toward or pushed away from the tuning bar so that the side walls can be tuned to have the precise distance therebetween for maximization of thermodynamic resonance therebetween.

The side walls, as well as the rear wall and roof of the enclosure preferably include a reflective surface comprised of a reflective material capable of reflecting infrared radiation. Hence, radiation from the incandescent light bulbs or other heat sources, as well as the occupants, is reflected off of the side walls and can resonate between the side walls of the enclosure. Preferably, this reflective surface is in the form of aluminum foil, copper foil or infra-red reflecting paint.

To reduce conduction heat transfer laterally within the side walls, preferably the reflective surface is broken up with gaps between separate regions of the reflective material. These gaps can be provided so that the reflective material is in the form of patches with gaps surrounding each patch, or in strips with more elongate gaps between the strips. Most preferably, conduction heat transfer within the side walls is encouraged by orienting the elongate reflective material vertically within an upper portion of the enclosure to help to draw heat from the light bulbs, which are typically located near the roof of the enclosure, down toward the head of the occupant when sitting in a chair within the enclosure (i.e. between a midpoint and two-thirds of the way from the floor to the roof of the enclosure).

Below a midpoint of the side walls, the strips are preferably oriented horizontally so that the gaps in the reflective material help to prevent further conduction heat transfer within the foil down lower into the enclosure. In this way, a perceived temperature within the enclosure is maximized around a head of the occupant to maintain the highest perceived temperature while actually maintaining a relatively lower temperature within the enclosure.

While the preferred enclosure is configured to receive an occupant in a seated position, the principles of this invention are equally applicable to enclosures which are configured best for a reclining or fully horizontal occupant, such as for sleeping. With the enclosure of this invention a relatively cool air temperature within the enclosure is maintained while a perceived temperature within the enclosure is comfortable for the occupant. An even lower temperature can be maintained outside the enclosure, such as within a room in which the enclosure is provided within a residence. In this way, only a minimal amount of energy is needed to maintain a comfortable environment inside the enclosure for the occupant of the residence.

OBJECTS OF THE INVENTION

Accordingly, a primary object of the present invention is to provide an enclosure in which a human occupant can comfortably reside with minimal energy expended to maintain a comfortable temperature within the enclosure, while uncomfortably low temperatures exist outside of the enclosure.

Another object of the present invention is to provide an enclosure which utilizes principles of thermodynamic resonance to maintain a warmer perceived temperature within the enclosure than would otherwise be experienced within the enclosure.

Another object of the present invention is to provide a thermodynamic resonance enclosure which is tunable to maximize the benefits of thermodynamic resonance within the enclosure.

Another object of the present invention is to provide a thermodynamic resonance enclosure which utilizes a minimum amount of energy to maintain a thermally controlled environment therein that is comfortable, while an environment outside of the enclosure is uncomfortably cool.

Another object of the present invention is to provide a thermodynamic resonance enclosure which can be constructed from readily available materials and which is easy to use with a minimum of construction experience required for the user.

Other further objects of the present invention will become apparent from a careful reading of the included drawing figures, the claims and detailed description of the invention.

DESCRIPTION OF THE PREFERRED EMBODIMENT

Referring to the drawings, wherein like reference numerals represent like parts throughout the various drawing figures, reference numeral 10 is directed to a thermodynamic resonance enclosure according to a preferred embodiment of this invention. The enclosure 10 provides a controlled thermal environment with a comfortable temperature for a human occupant therein while uncomfortably cool temperatures are maintained outside of the enclosure 10. The enclosure 10 thus decreases an amount of energy required to maintain a desired temperature within a residence by allowing only space within the enclosure 10 where the occupant is located to maintain a comfortable temperature.

Figure 1:
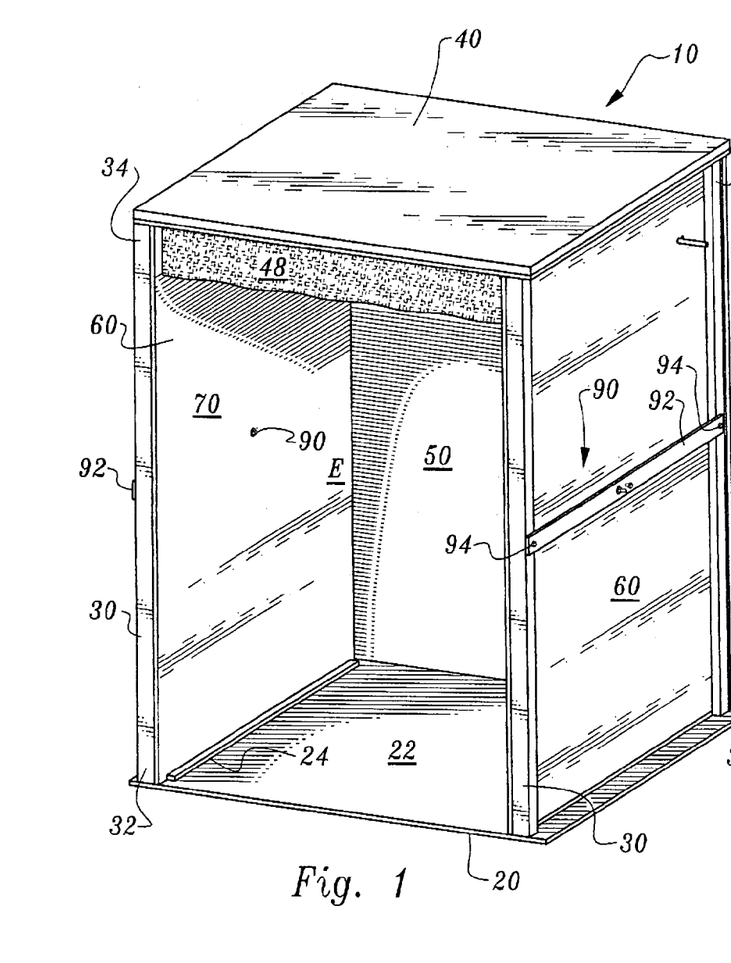
FIG. 1 is a perspective view of the thermodynamic resonance enclosure of this invention according to the preferred embodiment, and with the door removed.

In essence, and with particular reference to FIG. 1, basic details of the enclosure 10 are described. The enclosure 10 is preferably a generally rectangular hollow box surrounding the controlled environment E within the enclosure 10. The enclosure 10 preferably includes a base 20 upon which other portions of the enclosure 10 are supported. Corner posts 30 extend vertically upward from near corners of the base 20. A roof 40 rests upon upper ends of the corner posts 30 and is provided parallel with and spaced from the base 20 by a height of the enclosure 10. A rear wall 50 of generally planar form is provided extending in a vertical plane from the base 20 up to the roof 40. A pair of similar side walls 60 extend in parallel vertical planes from the base 20 up to the roof 40. At least one thermal source 80 (FIG. 3), such as an incandescent light bulb, is provided within the enclosure 10 to enhance an amount of heat originating within the enclosure 10. A door 100 (FIG. 2) is preferably provided hinged to one of the corner posts 30 and extending vertically between the base 20 and the roof 40 in a position generally parallel with the rear wall 50 when the door 100 is closed.

The side walls 60 are spaced apart by a distance equal to a whole number of half hydrogen cubits (a hydrogen cubit equal to 25.025 inches) to benefit from thermodynamic resonance between the side walls 60. The side walls 60 have a heat transfer optimization surface 70 which maximizes a rate of radiation heat transfer from the side walls 60 toward a center of the enclosure 10 near where a head of an occupant would be when the occupant is seated within the controlled environment E. This heat transfer optimization surface 70 includes material which is reflective of infrared radiation so that infrared radiation tends to remain within the enclosure 10 to maximize heat transfer into the occupant. The reflective material is broken up with gaps 76 to discourage conduction heat transfer within the side walls 60 themselves.

A width tuning system 90 is preferably provided to allow for precise tuning of an exact distance between the side walls 60. The width tuning system 90 preferably includes a tuning bar 92 extending horizontally between corner posts 30 adjacent each side of each side wall 60. Appropriate adjustable length fasteners preferably couple the tuning bar 92 to the side walls 60 so that the position of the side walls 60 can be slightly altered relative to each other. In this way, thermodynamic resonance between the side walls 60 can be maximized and the apparent heat experienced by the occupant within the enclosure 10 is also maximized.

The enclosure 10 provides a comfortable thermal environment therein for a human occupant even though the temperature within the enclosure 10 is somewhat less than a typically comfortable temperature and an air space outside of the enclosure 10 is significantly cooler than a comfortable temperature. The comfortable temperature controlled thermal environment E is thus provided with less energy expended to maintain this comfortable temperature within the environment E.

Figure 3:
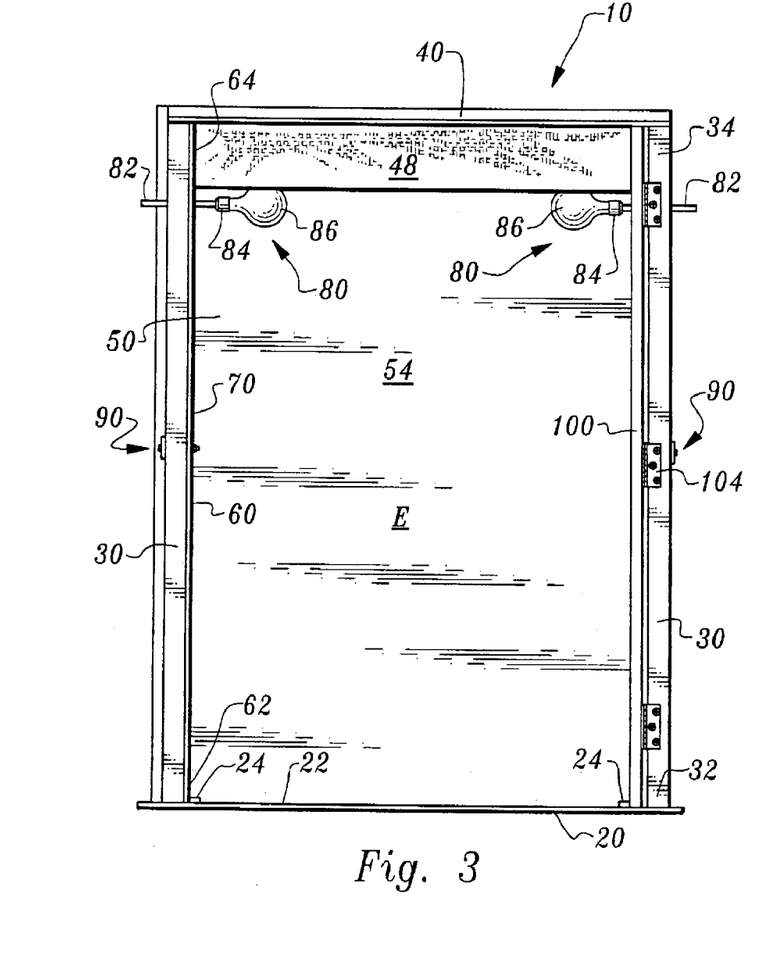
FIG. 3 is a front elevation view of that which is shown in FIG. 1 and with the door shown fully open.

More particularly, and with specific reference to FIGS. 1 and 3, details of the base 20, corner posts 30, roof 40 and rear wall 50 are described. These portions of the enclosure 10 along with the side walls 60 and door 100 provide the enclosure 10 in the general form of a hollow box. The base 20 is preferably provided upon which the entire enclosure 10 is supported, and helps to maintain a rigidity of the enclosure 10 and to allow for portability of the enclosure 10. The base 20 could alternatively be omitted with adjacent structures resting on or fixed to the ground.

The base 20 is preferably a planar horizontal thin rigid structure, such as a square of plywood or other planar cellulosic building material or non-cellulosic material (i.e. plastics, metal or composite material). Preferably, the width and depth of the base 20 are slightly greater than a width and depth of the enclosure 10. A thickness of the base 20 is not critical but is preferably approximately ½ inch.

The base 20 includes an upper surface defining a floor 22 of the enclosure 10. The floor 22 provides a surface upon which a chair can be placed to allow an occupant to be seated within the enclosure 10. The occupant could similarly stand or otherwise rest upon the floor 22. Linear strips 24 extend upon the floor 22 of the base 20 adjacent where the side walls 60 abut the base 20. The strips 24 help to securely hold the side walls 60 in a desired position where the side walls 60 abut the base 20.

Four corner posts 30 preferably extend vertically up from the base 20 near corners of the base 20. Each corner post 30 includes a lower end 32 abutting the base 20 and fastened to the base 20. Upper ends 34 of the corner posts 30 define ends of the posts 30 most distant from the base 20. Preferably, the corner posts 30 have a longest dimension similar to desired height for the enclosure 10. The corner posts are typically "2×2" wood posts, but could be other material or other sizes.

A roof 40 is coupled to the upper ends 34 of each of the corner posts 30. The roof 40 is preferably sized and shaped similar to the base 20 and oriented parallel with the base 20. The roof 40 thus encloses upper portions of the enclosure 10. Because heat rises, it is desirable that the roof 40 be configured in an insulated fashion to minimize heat transfer out of the enclosure 10 through the roof 40.

Specifically, the roof 40 preferably includes multiple layers. A structural layer 42 typically of ¼ inch thick rigid board material is provided abutting the upper ends 34 of the corner posts 30. The roof 40 additionally includes a reflective surface 44 on a lower side of the structural layer 42. This reflective surface 44 is preferably provided with a reflective foil material (i.e. copper or aluminum foil) or other material which is reflective of electromagnetic radiation, and especially infrared radiation striking the reflective surface 44. An insulation layer 46 is preferably provided above the structural layer 42. The insulation layer 46 is constructed of a material which impedes the transfer of heat therethrough. Preferably, the insulation layer 46 is in the form of a planar sheet of foam material having a high "R-value" indicative of a relatively great thermal resistance.

Preferably, a curtain 48 extends down from an edge of the roof 40 on a forward side of the enclosure 10. The curtain 48 extends downward from the roof 40 and tends to prevent hot air within the enclosure 10 from escaping out of the enclosure 10 when no door is provided or when the door 100 (FIG. 2) is opened.

The rear wall 50 is a planar rigid structure extending between the two corner posts 30 on a rear portion of the enclosure 10 and extending up from the base 20 to the roof 40. Preferably, the rear wall 50 entirely encloses the rear side of the enclosure 10. The rear wall 50 is preferably provided with multiple different layers to assist in maximizing retention of heat within the enclosure 10 and minimizing heat transfer through the rear wall 50. Specifically, a rigid structural layer 52 formed of a thin board material such as plywood provides for structural support within the rear wall 50. A reflective surface 54 is provided on a side of the rear wall 50 facing the controlled thermal environment E within the enclosure 10. This reflective surface 54 can be formed by providing a foil of material (i.e. copper or aluminum) reflective of electromagnetic radiation, and particularly infrared radiation. An insulation layer 56 is preferably provided on a side of the structural layer 52 opposite the reflective surface 54. The insulation layer 56 can be configured similar to the insulation layer 46 of the roof 40, such as formed of a planar sheet of foam having a relatively high "R-value."

Figure 4:
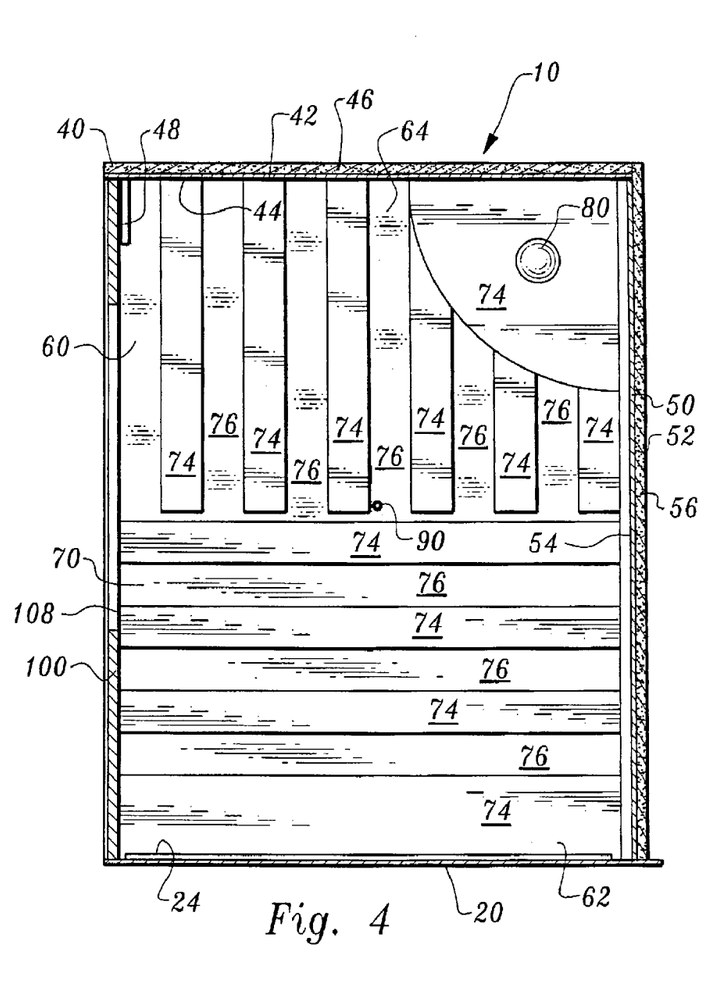
FIG. 4 is a side elevation full sectional view of that which is shown in FIG. 2 and illustrating a preferred form of reflective surface for the side walls of the enclosure.

With particular reference to FIGS. 3 and 4, details of the side walls 60 of the enclosure 10 are described. The side walls 60 are provided not only to complete the enclosure 10 and assist in retaining heat within the enclosure 10, but also the side walls 60 are particularly configured to maximize thermodynamic resonance within the enclosure 10. The side walls 60 thus help to maximize the temperature apparent to an occupant within the enclosure 10.

Figure 6:
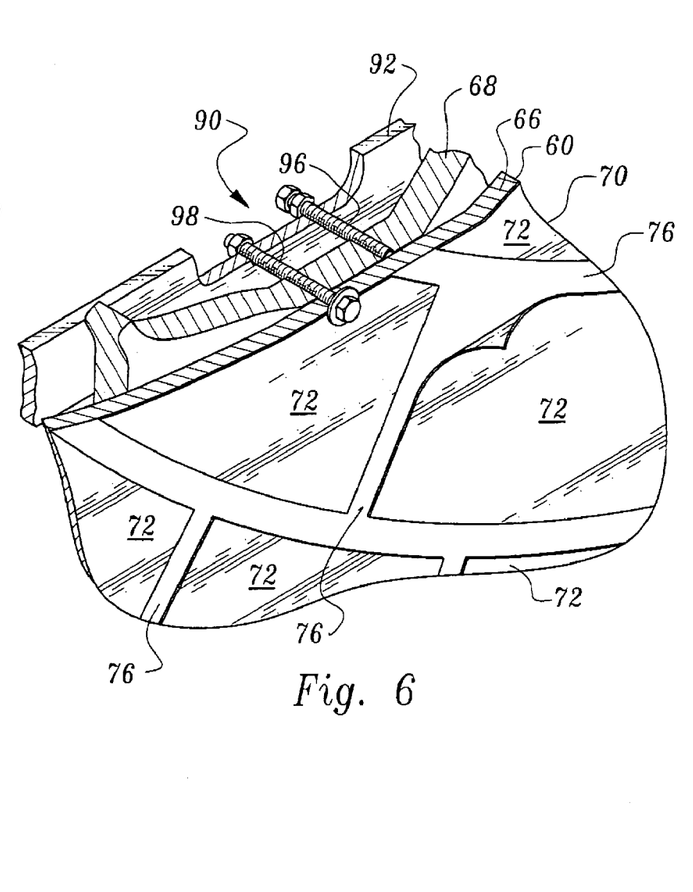
FIG. 6 is a detail of a portion of that which is shown in FIG. 5 revealing details of the reflective material thereof and the width tuning system according to this invention.

The side walls 60 are each generally planar in form and oriented parallel with each other and preferably within a vertical plane. The side walls 60 include bottom edges 62 adjacent the base 20 and top edges 64 adjacent the roof 40. As with the rear wall 50, the side walls 60 preferably each include a structural layer 66 and an insulation layer 68 (FIG. 6). The structural layer 66 is preferably substantially rigid, but exhibits some flexibility when forces are applied. Most preferably, the structural layer 66 of the side wall 60 is formed of ¼ inch board material such as plywood.

Preferably, a majority of the weight of the enclosure 10, and particularly the roof 40 and upper portions of the rear wall 50 and side walls 60 are supported in position primarily by the strength of the corner posts 30 to which the roof 40, rear wall 50 and side walls 60 are attached, rather than being primarily supported by the strength of the rear wall 50 and side walls 60 themselves. In this way, the rear wall 50 and side walls 60 can be formed of relatively thin materials so that the entire enclosure 10 is less heavy to facilitate ease in shipping and movement within a residence where the enclosure 10 is located. Also, the relatively thin structural layer 66 in each side wall 60 facilitates width tuning of the side walls 60 according to the width tuning system 90 discussed in detail below, to maximize thermodynamic resonance in the enclosure 10.

Figure 5:
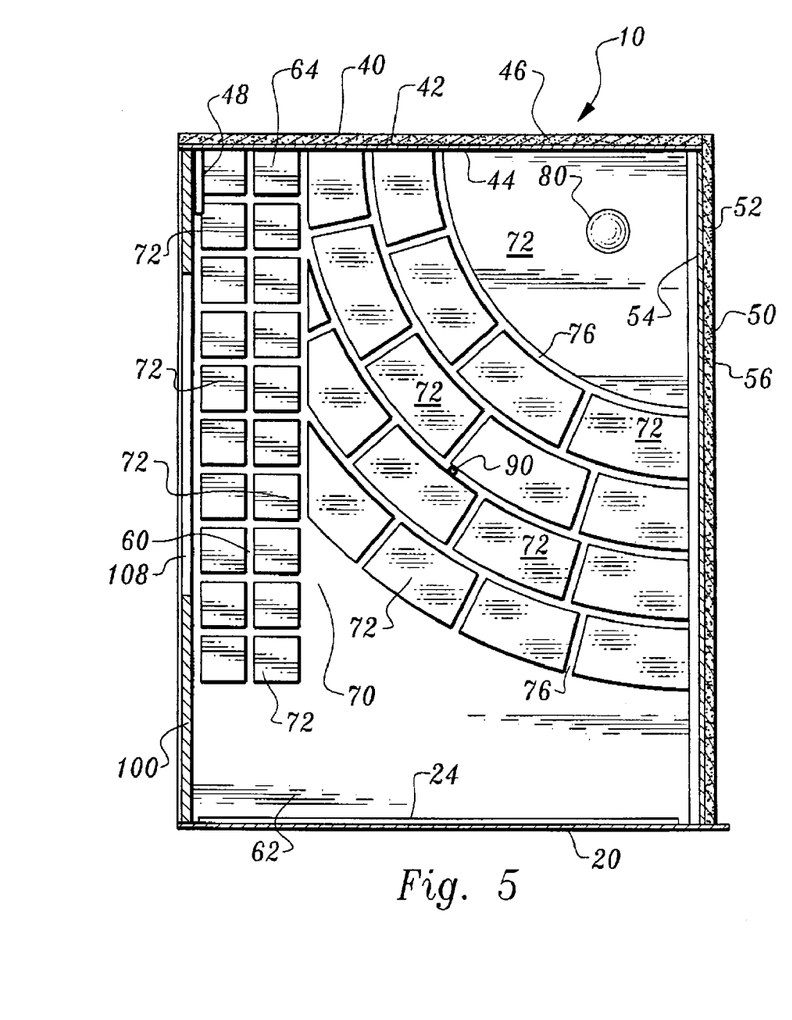
FIG. 5 is a side elevation full section view of an alternative embodiment of that which is shown in FIG. 4 with an alternative pattern of reflective material in the form of patches.

The side walls 60 preferably support both a heat transfer optimization surface 70 and a thermal source 80. Specifically, the heat transfer optimization surface 70 is provided on a portion of each side wall 60 facing the opposite side wall 60. This surface 70 is preferably in the form of reflective strips 74 located on the side walls 60 with the strips 74 spaced apart by gaps 76. As an alternative, reflective patches 72 can be provided (FIGS. 5 and 6). The pattern of the reflective strips 74 or reflective patches 72 can exhibit a variety of different patterns with gaps 76 therebetween. However, most preferably the reflective strips 74 are particularly oriented to maximize an apparent temperature experienced by the occupant within the enclosure 10.

Specifically, a lower portion of the side wall 60 is provided with reflective strips 74 which have a longest dimension extending horizontally, and with gaps 76 between adjacent reflective strips 74. Upper portions of the side walls 60 are provided with similar reflective strips 74 but with a longest dimension oriented vertically with gaps 76 therebetween. Portions of the side walls 60 closest to where the thermal source 80, such as an incandescent light bulb, are located preferably to include a large quarter-circular panel of reflective strip 74 material.

The orientation of the elongate reflective strips 74 maximizes an apparent temperature for an occupant within the enclosure 10 in the following manner. The reflective strips 74 are preferably formed of a material such as copper foil or aluminum foil. Such materials are highly reflective of electromagnetic radiation, and particularly infrared radiation. Hence, electromagnetic radiation from the incandescent light bulb 80 or other thermal source 80 and infrared radiation from the opposite side wall 60 and from the occupant which impact the reflective strips 74 are largely reflected back away from the side wall 60 supporting the heat transfer optimization surface 70 including the reflective strips 74. This reflection desirably increases an apparent temperature felt by the occupant within the enclosure 10.

Disadvantageously, such reflective foils as copper foil and aluminum foil also readily transfer heat by conduction laterally within the foil forming the reflective strips 74. It is desirable to maximize heat flow toward a head of the occupant within the enclosure 10 which would typically be located slightly above a vertical midpoint within the enclosure 10. It is undesirable to encourage heat transfer away from this region and down to the base 20. Additionally, it is desirable that the thermal source 80 in the form of an incandescent light bulb be located near the roof 40 so that the thermal source 80 in the form of a light bulb can also provide light, such as for reading within the enclosure 10, and to take advantage of projection of infrared radiation by locating the thermal sources 80 symmetrically within corners of the enclosure 10.

Because the air within the enclosure 10 will tend to rise due to natural convection forces and because the thermal sources 80 are located near the roof 40, it is desirable to encourage conduction heat transfer within the reflective strips 74 down from the roof 40 toward a midpoint in the height of the enclosure 10 and near a head of the occupant. It is desirable to discourage lateral heat transfer in this upper portion of the enclosure 10 toward the front of the enclosure 10 or the rear wall 50 of the enclosure 10 which would be generally away from the occupant within a center of the enclosure 10. Hence, the reflective strips 74 are oriented vertically with at least small vertical gaps 76 therebetween. The vertical gaps 76 discourage conduction heat transfer laterally within an upper portion of the enclosure 10 and the vertical reflective strips 74 encourage conduction heat transfer downward vertically to a region closer to a head of the occupant within the enclosure 10.

Below the midpoint of the enclosure 10, it is desirable to discourage further downward vertical conduction heat transfer within the reflective strip 74. Hence, the reflective strips 74 within a lower portion of the enclosure 10 are oriented with a longest dimension extending horizontally and with horizontally extending gaps 76 between the reflective strips 74 to discourage conduction heat transfer vertically downward toward the base 20. The heat transfer optimization surface 70 additionally includes the quarter-circular reflective strip material 74 located adjacent the thermal sources 80 to encourage radiation heat transfer out of the corners where the thermal sources 80 are located, and generally in the direction toward the head of the occupant within the enclosure 10.

In FIG. 5 reflective patches 72 are provided with gaps 76 therebetween. These reflective patches 72 generally are arrayed arcuately away from the thermal source 80. The reflective patches 72 have gaps 76 therebetween but cover a majority of the surface of the side walls 60. In this alternative embodiment of FIG. 5 reflection of infrared electromagnetic radiation is maximized while conduction heat transfer laterally both vertically and horizontally within the side walls 60 is discouraged so that heat is not drawn toward the base 20 or roof 40, or toward the front or rear of the enclosure 10 in an undesirable fashion. The reflective patches 72 would typically be formed from a similar foil material as that provided with the reflective strips 74 of the preferred embodiment shown in FIG. 4.

The thermal sources 80 are preferably in the form of incandescent light bulbs which provide both a light source and emit significant amounts of infrared radiation to direct heat toward the occupant within the enclosure 10. The thermal source 80 includes a socket 84 with electric wire 82 extending thereto and with a bulb 86 coupled to the socket 84 for operation according to this invention. If light is not required within the enclosure 10, other forms of thermal sources 80 could be provided, such as high temperature fluid flow containing radiators, electrical resistance coils, or other high temperature structures.

With particular reference to FIGS. 1 and 6, details of the width tuning system 90 are described. The width tuning system 90 provides for tuning a precise distance between the side walls 60 to maximize thermodynamic resonance between the side walls 60. Particularly, it is desirable that the heat transfer optimization surfaces 70 of each side wall 60 be spaced precisely apart according to the equation:

$$X=n(25.025 \text{ inches})/2 \quad \text{(equation 1)}$$

In equation 1 "X" is the distance between the side walls 60 and "n" is a positive whole integer. 25.025 inches is also referred to as one "hydrogen cubit" and 25 "hydrogen inches."

In essence, spacing the side walls 60 apart a distance which substantially equals a multiple of half hydrogen cubits causes infrared radiation within the enclosure 10 to resonate between the side walls 60 so that a maximum apparent temperature is experienced by an occupant between the side walls 60 and within the enclosure 10. While the side walls 60 could be precisely located in their desired position as an acceptable alternative, such precise construction would be difficult to achieve and subject to some variation during collapse and redeployment of the enclosure 10, and when the enclosure 10 experiences dimensional modification such as due to thermal expansion forces. To avoid the need to precisely construct the enclosure 10 it is desirable according to the preferred embodiment that a width tuning system 90 be provided so that the width of the enclosure 10 can be precisely tuned after construction is complete.

Specifically, the width tuning system 90 preferably provides a means to tune a precise distance between the sidewalls 60. Preferably, the tuning means includes a tuning bar 92 extending horizontally between the corner posts 30 adjacent each side wall 60 and near a vertical midpoint in the side walls 60. The tuning bars 92 are on outside edges of the corner posts 30 so that the tuning bars 90 are spaced slightly away from the side walls 60. Each tuning bar 92 is advantageously a substantially rigid metal bar. However, some effectiveness can be obtained even if the tuning bar 92 is of similar rigidity to the materials forming the side walls 60 or even less rigidity.

At least one adjustable length fastener, or some other form of means to adjustably connect the side walls to the tuning bar, couples a midpoint of each tuning bar 92 to the adjacent side wall 60. While it is only strictly necessary that one of the side walls 60 include a width tuning system 90, preferably each of the side walls 60 include such a width tuning system 90. The length adjustable fastener is preferably in the form of at least one bolt rotatably coupled to the side wall 60 with a threaded shaft of the bolt passing through a threaded bore adjacent to the tuning bar 92. For instance, a hole can be drilled and threaded in the tuning bar 92, or a nut can be welded to the tuning bar 92 adjacent the hole so that the bolt passes through this nut adjacent the tuning bar 92. A head of the bolt can be rotatably supported adjacent the side wall 60. In this way, as the bolt is rotated, relative to the side walls 60, the head of the bolt remains adjacent the side wall 60 but the threaded shaft of the bolt is caused to be drawn through the threaded bore and the nut adjacent the bar 92 so that the bolt draws the side wall 60 either toward the tuning bar 92 or away from the tuning bar 92 depending on the direction in which the bolt is rotated.

In a form such as that shown in FIG. 6, two bolts are provided including a narrowing bolt 96 and a widening bolt 98. In this configuration the nut of the widening bolt 98 need not be captured to the tuning bar 92. The narrowing bolt 96 has a nut captured to the tuning bar 92 and a head of the bolt 96 is on a side of the tuning bar 92 opposite the side wall 60. As the narrowing bolt 96 is appropriately rotated, it passes further through the tuning bar 92 with a tip of the threaded shaft of the narrowing bolt 96 abutting the side wall 60 and pushing the side wall 60 toward the opposite side wall.

The widening bolt 98 is oriented with the head of the widening bolt 98 within the enclosure 10 and adjacent the side wall 60. The threaded shaft of the widening bolt 98 extends through a hole in the side wall and then through a hole in the tuning bar 92 with a nut on an exterior of the tuning bar 92. As the widening bolt 98 is rotated, it is drawn toward the tuning bar 92 so that the side wall 60 is drawn away from the opposite side wall. Thus, this two bolt 96, 98 arrangement of the width tuning system 90 provides the embodiment, as particularly depicted in FIG. 6.

While bolts have been described as the adjustable length fastener for the width tuning system 90, various different adjustable coupling means can be provided with bolts merely providing one form of such adjustable length coupling means. For instance, wedges could be provided which would be wedged between the tuning bar 92 and the side wall 60 to adjust slightly the position of the side walls 60 relative to each other. Turnbuckle type devices could be utilized which would adjust in length when rotated and oriented between the tuning bar 92 and the side wall 60. Wire connectors between the tuning bar 92 and the side walls 60 could be provided which when twisted would adjust slightly in length and other fasteners, either manual or powered, having the ability to couple two structures together and adjust a distance between those structures could similarly be substituted for the bolts according to the preferred embodiment of this invention.

Figure 2:
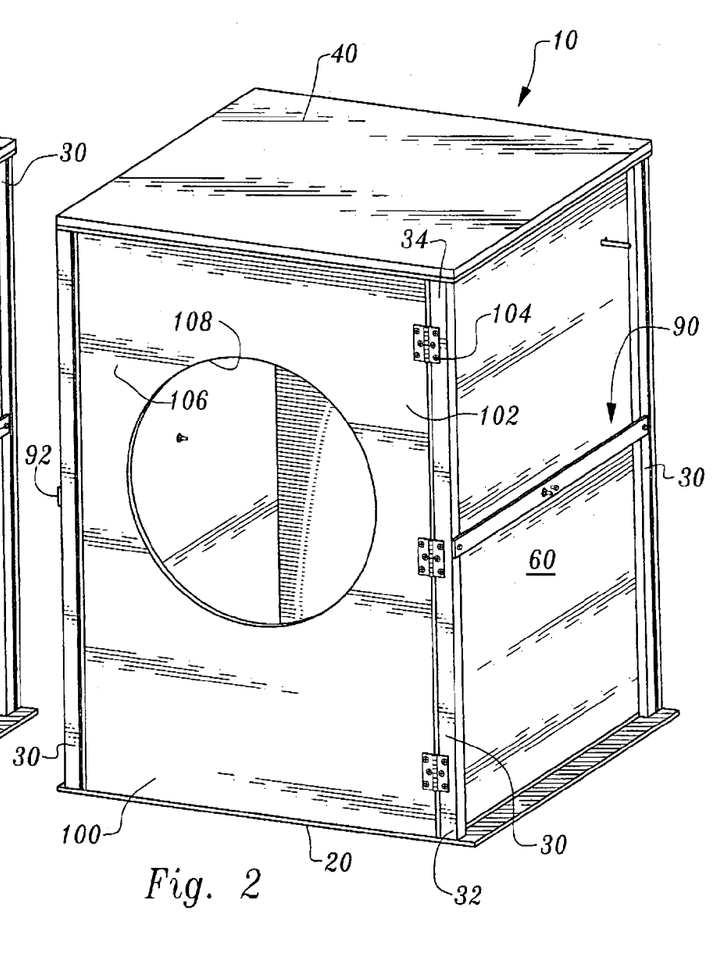
FIG. 2 is a perspective view of that which is shown in FIG. 1 with the door included thereon.

With particular reference to FIGS. 2–4, details of the door 100 of the enclosure 10 are described. The door 100 is not strictly necessary, with significant benefit being provided even when the door 100 is open or omitted altogether. The door 100 allows for maximization of retention of heat within the enclosure 10 to obtain the maximum benefit according to this invention. The door 100 preferably includes an attached edge 102 coupled through hinges 104 to one of the corner posts 30. A free edge 106 is spaced from the attached edge 102 a sufficient distance so that the door 100 preferably almost entirely closes off a front side of the enclosure 10 with some space preferably provided for ventilation. A window 108 is preferably provided within the door 100 to allow for a maximum amount of typical residential activities to be enjoyed by the occupant within the enclosure 10, including watching television, and otherwise observing activities within the room in which the enclosure 10 is located. If desired, the door 100 can be insulated and fitted with reflective material on its inner surface.

With particular reference to FIGS. 1–4, details of the use and operation of this invention are described. Initially, the enclosure 10 is constructed preferably as shown. Once initial positioning of the major structures of the enclosure 10 have been completed, the enclosure 10 is preferably tuned to maximize thermodynamic resonance within the enclosure 10. Specifically, the user can take a careful measurement of a distance between the side walls 60. This distance can be compared with a desired number of half hydrogen cubits to be provided between the side walls 60. The width tuning system 90 is then utilized as discussed in detail above to bring the side walls 60 closer to each other or further away from each other until the precise distance between the side walls 60 is obtained.

Alternatively, the occupant can sit within the enclosure 10 and adjust the width tuning system 90 from within the enclosure until the occupant perceives the maximum temperature within the enclosure 10 due to the phenomena of thermodynamic resonance being maximized within the enclosure 10. Once tuned, the enclosure 10 typically would not require retuning, unless for some reason it comes out of adjustment.

The user would, before or after tuning, couple the thermal sources 80 to a source of power and turn on the current so that the thermal sources 80, typically in the form of incandescent light bulbs commence electromagnetic radiation, and particularly infrared radiation within the enclosure 10. The user can either close the door 100 and wait for the enclosure 10 to heat up somewhat, or can enter the enclosure 10 while the enclosure 10 and the controlled thermal environment E therein increases in temperature.

The thermal sources 80 radiate infrared radiation therefrom which is reflected off of the roof 40, rear wall 50 and side walls 60 in a manner generally toward the head of the occupant within the enclosure 10. Additionally, thermodynamic resonance between the side walls 60 and within the corner cube reflectors, described in detail in the examples below, maximize the phenomena of thermodynamic resonance, particularly in proximity to the head of the occupant user within the enclosure 10.

Typically, an occupant who would normally be comfortable in a 70° F. environment would begin to feel that the temperature is comfortable when an actual measured temperature within the enclosure 10 is between 66° F. and 68° F. Due to the insulation of the enclosure 10, this desired temperature can be readily obtained and maintained, typically with two incandescent light bulbs of relatively low wattage (i.e. 60 watts to 95 watts). Additionally, the occupant emits infrared radiation which is largely reflected back at the occupant to maintain the perception of comfortable temperature within the enclosure 10. Outside the enclosure 10, the temperature can be 60° F. or lower while still maintaining a desired comfortable controlled thermal environment E within the enclosure 10. The residence outside the enclosure 10 can thus be readily maintained at a low temperature with minimal expenditure of energy while a comfortable environment is provided within the enclosure 10 for the occupant.

The invention is further described with reference to the following specific examples and specific definitions.

DEFINITIONS

The hydrogen inch (H. I. or H") is defined as one of the wavelengths of the hydrogen atom and is equal to 1.001 American inches. The scientific reference, PSUF ("Pyramid Science and the Unified Field, Second Edition," by Walter F. Dimmick, copyright 1996), explains how the hydrogen inch is derived from the hydrogen 21 centimeter or 8.3 inch spectral line which has a frequency of 1420.4056 megahertz.

The hydrogen cubit (H. C.) is defined as 25 hydrogen inches or 25.025 American inches.

Thermodynamic resonance is defined as the principle of causing a radio frequency cavity, box or room having interior dimensions in multiples of half of the hydrogen cubit or half the hydrogen inch to oscillate or resonate and to make the box feel warmer to the occupant and also to help warm up the interior air of the box.

Bioelectric waves or the bioelectric components of an electromagnetic wave are defined as the electromagnetic waves from living things. Also, substances containing hydrocarbons exhibit these bioelectric waves. These bioelectric waves, their characteristics and methods of detection, generation and method of measuring their wavelengths, etc. are explained in great detail in the PSUF scientific reference.

EXAMPLE 1

An enclosure has interior dimensions of 1.5 hydrogen cubits (H. C.) or approximately 37%16 inches in width, 2.5 hydrogen cubits (H. C.) or approximately 62%16 inches in height and 1.5 hydrogen cubits in depth. The sides and rear wall consist of ½ inch thick composition board with a paper veneer-like finish. The interior of the side is lined with 0.006 inch thick copper foil. The interior is partially lined with 0.006 inch thick copper foil consisting of an 18.75 inch radius quarter circle in the upper rear corner, plus vertical four inch wide strips of copper foil and horizontal four inch wide strips of copper foil. The interior of the back of the box is partially lined with 0.006 inch thick copper foil consisting of two 18.75 inch radius quarter circles, one in each upper corner of the back of the box. The remainder of the back of the interior of the box is lined with a heat reflecting material consisting of 0.0005 inch thick plastic, coated with aluminum or silver (silver plastic). The front of the box is open. The floor consists of bare plywood approximately ½ inch thick. The top of the box is similar to the sides and back made of ½ inch thick composition board with the interior partially lined with 0.006 inch thick copper foil. The quarter circles and wall of copper foil on the interior of the sides, back and ceiling of the box constitute 18.75 inch radius "corner cube reflectors" (CCRs) in each upper rear corner of the box. The top, sides and back of the box are insulated on the outside with sheets of one inch thick polystyrene foam plastic.

Incandescent electric bulbs are installed in each of the upper rear corners of the interior of the box. The corner cube reflector is useful in focusing the heat energy from the light bulb out along the central axis of the corner cube reflector (CCR) and a few degrees of arc on each side of this central axis of the CCR. Each light bulb is installed at approximately 7.5 inches from each wall and ceiling of the box so that the center of the bulb or filament thereof is approximately 12.5 inches from the apex of the CCR. Thus, the bulb is at or near the focus of the CCR. The wattage size of the incandescent light bulbs are selected to achieve the desired heating of the box. In this example, each bulb is a white frosted 60 watt incandescent bulb. The two light bulbs also provide a good reading light for the occupant of the box.

The interior side walls are spaced apart in a multiple of ½ hydrogen cubits. It is known in radio engineering that a one half wavelength spacing between radiating elements produces reflection of that radio wave. This principle is used in the design of radio antennas, radio wave reflectors, microwave resonant cavities and the like. This same principle of half wavelength reflection is used in optics to produce reflectors such as mirrors, laser components and the like. On the other hand, ¼ wavelength or odd multiples thereof are used to produce absorption rather than reflection of a radio wave. This principle is used in antenna design and electric wave filter design, for example. In optics, a ¼ wavelength (or odd multiple thereof) coating on a lens will reduce the normal light reflection of a glass lens, increase the light transmittance of the lens and make the lens more efficient.

I have discovered in my research that a burning candle emits electromagnetic waves and bioelectric waves that measure one hydrogen inch, one half hydrogen cubit, one hydrogen cubit, plus many other wavelengths. I have also discovered in my research that the human body emits electromagnetic and/or bioelectric waves of one hydrogen inch, one half hydrogen cubit, one hydrogen cubit, plus many other wavelengths. This is not surprising since the principle component of the human body is water and the principle component of water is hydrogen.

I have also discovered in my research that a tungsten light bulb emits electromagnetic and bioelectric waves that are similar in wavelength to the hydrogen inch and hydrogen cubit. For example, the corner cube reflector with an illuminated tungsten bulb disposed at or near the focus of the corner cube reflector produces electromagnetic standing waves having electromagnetic field lines transverse to the central axis of the CCR at approximately eight inches from the tungsten filament, a broad band of transverse field lines between 20 and 25 inches from the tungsten filament, and other E. M. field lines at about 34 inches, 39¾ inches from the tungsten filament, plus other field lines. These standing waves conduct heat from the bulb along the waves.

The enclosures of this invention are designed to have widths and heights that are multiples of ½ hydrogen cubits. Thus, if a human occupant sits between these walls the walls reflect back the hydrogen inch waves and hydrogen cubit waves emitted from the occupant's body. This tends to make the human body feel warmer in a cool environment and it appears to contribute a little (about one or two degrees of temperature) to warming up the air in the box/enclosure.

The copper foil on the walls performs two functions, one desirable for warming up the box and its occupant and one working against heating up the occupant of the box. The copper foil reflects the heat energy from the human body and from the light bulbs which is desirable for making the occupant feel warmer and in warming up the interior of the box. As well as being a good reflector of heat, the copper foil is also a good conductor of heat so it conducts the heat away from alongside the occupant or the light bulbs. The copper wall always feels cold or cool to the touch and therefore tends to draw heat out of the human body. If heat is being drawn out of the human body, the body tends to feel cold. To alleviate this problem in this example the copper foil on one side wall is divided into strips of about four inches in width. The copper still reflects heat energy across the width of the enclosure but it cannot conduct heat away as far as with a solid wall of copper. In this embodiment the four inch wide copper strips in the top half of the wall are disposed vertically. By convection the top of the box is warmer than the bottom of the box. The copper strips are warmed by radiation from the occupant and from the light bulbs and warmed by convection from the warmer air in the top of the box. The heat is conducted down the copper strips to warm the strips opposite the occupant to make him feel more comfortable.

The copper strips in the lower half of the wall are disposed horizontally. Thus, they can reflect heat back and forth across the box but not conduct heat very far down the box away from the occupant's torso. In this example of the enclosure, one side wall uses solid copper foil as a covering and the opposite side wall uses four inch wide strips of copper foil. The solid copper foil covered wall always feels cold to the touch while the copper strips on the opposite wall always feel warmer to the touch than the solid copper foil wall. This demonstrates that the heat reflecting wall feels more comfortable if it is broken up into strips or in some other pattern. A cloth curtain approximately six inches long is suspended from the top of the open front of the box.

A chair on casters for the occupant is placed in the center of the box. The chair is a comfortable chair with a high back, to help keep the occupant's back warm.

A thermometer is mounted at about the middle of the interior of the left wall.

In operation, the desired room temperature outside the box/enclosure is 60° F. or near that. The occupant records the outside room temperature and the inside the box temperature. The occupant turns on the two 60 watt lights and sits inside the box. Even at 60° F. air temperature inside the box the beams from the two corner cube reflector lights strike the back of the occupant's head and he immediately feels somewhat warm if not entirely comfortable. The copper ceiling of the corner cube reflector above the light bulbs starts to heat up. Initially the air temperature inside the box starts to heat up about one degree every two minutes. By the time the air temperature inside the box gets up to about 65° F., the box starts to feel comfortable. This comfortable temperature will no doubt vary with the occupant.

The occupant feels comfortable at this modest temperature, because the side walls are reflecting his body heat back to his body. The copper ceiling is being warmed by radiation from the hot light bulbs and by convection heat rising from the hot bulbs and from the occupant. The remainder of the copper ceiling feels cold to the touch. Heat from the copper ceiling above the bulbs is conducted along the copper ceiling and after a few minutes the copper ceiling above the occupant's head feels warmer and this contributes to the comfortable feeling of the occupant. The copper foil wall on the left (looking out of the box) always feels cold which means it is drawing heat out of the body as well as reflecting heat back to the body. The copper foil on the right wall which is divided into strips does not feel as cool to the touch as the left wall. The right wall is reflecting heat back to the body but is obviously not drawing as much heat out of the body as the left copper wall. The occupant's back always feels warm because of the high back chair but the back of the neck feels cool as it is exposed to the uncovered back wall. The back of the neck feels warm when the back wall is lined with heat reflecting material such as silver plastic which reflects the heat back to the body.

After the occupant sits in the box for about twenty minutes the air temperature rises about 7° F. or 8° F. to 67° F. or 68° F. and the occupant feels comfortable even though the room temperature outside the box is at 60° F. The front of the box is open for ventilation and the small curtain 48 across the top of the open front of the box reduces the flow of warm air from the box. If the occupant and chair are removed from the box and replaced by a 75 watt light bulb, the heating results are almost the same as with the occupant and chair in the box. One of the applications of this box is to save heating energy for a house by turning down the thermostat to 60° F. for the entire house and sitting in the enclosure which only uses 120 watts for heating and lighting.

EXAMPLE 2

A second enclosure is provided larger than the box/enclosure of example 1. This box has interior dimensions of two hydrogen cubits or about 50¹/₁₆ inches wide, 2½ hydrogen cubits or about 62⁹/₁₆ inches high and about forty-eight inches long. This box has a front door which closes most of the front of the box but leaving approximately a two inch wide slit at one side of the door for ventilation. The door is hinged at one side to provide easy access to the box. The door has a forty-two inch diameter circular window disposed about at the center of the door. The door is made of approximately ½ inch thick plywood and the window is ½ inch thick glass. The sides and rear wall of the box are made of ¼ inch thick pressed hard board referred to by the trademark Masonite.

One inch thick polystyrene foam plastic sheets are cemented to the exterior of these Masonite panels for insulation. Since the Masonite panels have a tendency to warp or oil-can a little, means are provided for moving the center of the outside of the side panels in or out to provide accurate spacing of the two hydrogen cubit interior width dimension. The ceiling of the box is made of ¼ inch Masonite with one inch thick polystyrene foam insulation cemented to the top of it. The interior of the ceiling is lined with 0.035 inch thick sheet copper. To prevent sagging of the ceiling, reinforcing cross bars are fastened to the outside of the top of the ceiling panel. The floor of the box is approximately ½ inch thick plywood.

The interior of the right side wall has a ¾ hydrogen cubit (approximately 18.75 inches) radius 0.006 inch thick copper foil quarter circle, fastened to the upper rear corner to form part of a corner cube reflector (CCR). Surrounding the quarter circle is an approximately one inch wide space with no metal foil. Surrounding this space is a ¼ hydrogen cubit (approximately 6¼ inches) wide quarter circle, of 0.0005 inch thick aluminum foil. This ¼ hydrogen cubit wide band of aluminum foil is divided into sectors 6¼ inches to ten inches wide with approximately one inch wide spaces between the sectors, to cause discontinuity of this band of aluminum foil (see FIG. 5). Next is another approximately one inch wide band with no aluminum foil. Several concentric circles, ¼ hydrogen cubit in width broken into six to ten inch wide sectors are disposed around the ¾ hydrogen cubit radius quarter circle to cover a large part of the interior of the right wall. Part of the interior of the right wall is covered with ¼ hydrogen cubit (H.C.) 0.0005 inch thick aluminum foil squares separated from each other by approximately ½ inch. These aluminum quarter circles and squares cover most of the interior of the side.

The interior of the left wall has a ¾ hydrogen cubit (approximately 18.75 inches) radius 0.006 inch thick copper quarter circle fastened to its upper rear corner of the wall to form part of a corner cube reflector (CCR). The interior of the left wall that is not covered by the copper foil quarter circle is lined with 0.0005 inch thick aluminum foil. This covers most of the interior surface of the wall.

The interior of the rear of the box has two ¾ hydrogen cubit radius 0.006 inch thick quarter circles of copper fastened in the upper rear corners. The copper lining of the ceiling and the quarter circles of copper foil in the upper rear corners of the box constitute two corner cube reflectors in the upper rear corners of the box. Incandescent light bulbs and are mounted at approximately 7.5 inches from the ceiling, 7.5 inches from the side panel and 7.5 inches from the rear panel in each CCR. This places the light bulb filament at about 12.5 inches or ½ hydrogen cubit from the apex of the CCR which is about at the focus of the CCR. Most of the remainder of the back wall that is not covered by the copper foil quarter circles is lined with an infrared or heat reflecting material which consists of 0.0005 inch thick sheet plastic covered with a thin coating of silver or aluminum.

Aluminum is a good reflector of infrared or heat energy. Aluminum is also a good conductor of heat energy. The interior of the right wall is also largely covered with 0.0005 inch thick aluminum foil. This is done to provide a good reflecting surface for the infrared or heat energy emanating from the human occupant and the light bulbs. To reduce the conduction of heat by the aluminum foil the foil is broken up into various patterns. This pattern consists of one quarter hydrogen cubit (approximately 6¼ inches wide) concentric circular bands surrounding the quarter circle of the corner cube reflector. There is an approximately one inch spacing between the concentric bands of aluminum foil. Each concentric band of aluminum foil is in turn broken up into sectors that are approximately 6¼ inches to ten inches long and separated by approximately one inch spacing. Part of the right wall is covered with ¼ hydrogen cubit (approximately 6¼ inches) squares of 0.0005 inch thick aluminum foil that are separated by approximately one half inch on all sides from the next aluminum foil square or aluminum foil tile.

In operation of this second example box/enclosure, one turns on the 95 watt bulb in the upper left (looking out) rear corner and the 60 watt bulb in the upper right rear corner of the box providing a total of 155 watts for lighting and heating of the box. The occupant then sits in the large swivel castered chair inside the box and closes the front door. The occupant provides about the equivalent of a 75 watt light bulb for space heating. A thermometer is disposed on the interior of the left wall at about the center of the wall and a similar thermometer is placed outside the box to read the room temperature. A clock is taken inside the box. The initial interior temperature of the box is the same as the outside the box room temperature and the experiments are usually started at or near 60° F.

The warm beams from the CCRs strike the occupant's head and the occupant immediately feels somewhat warm even in the 60° F. box. The light bulbs also radiate heat upward. The heat radiation and the hot air convection soon heats the 0.035 inch thick copper ceiling above the light bulbs. There is more thermal inertia and heat storage capacity in the 0.035 inch thick copper ceiling used in the box of this second example than in the 0.006 inch thick copper ceiling used in the box of the first example above. Initially the air temperature of the box rises at about one degree every two minutes. One's back immediately feels warm because it is against the back of the chair. The back of the occupant's neck initially feels cool until an infrared reflector consisting of 0.0005 inch thick plastic with a thin coating of infrared reflecting material such as silver or aluminum is fastened to the back wall.

The side walls are receiving heat energy from the occupant and from the CCRs and light bulbs and the side walls being spaced two hydrogen cubits apart reflect this heat energy back and forth to make the occupant feel warm and comfortable and to augment the efficient space heating of the box. I have defined this reflecting of heat energy back and forth between infrared reflecting surfaces that are spaced in multiples of one half hydrogen cubit, "thermodynamic resonance."

When the air in the box heats up to about 65° F. the occupant feels comfortable even if the air temperature is still relatively cool. The feeling of comfort is attributed to the thermodynamic resonance heating inside the box, to the CCR beam heating of the back of the head and to the reflection of the body heat from the back of the neck from the infrared reflector material on the back wall. This infrared reflecting material reflects about ninety percent of the infrared energy striking it. After about twenty minutes the heat that has warmed the copper ceiling above the light bulbs has been conducted to the center of the ceiling so the ceiling feels warm above the head. This contributes to the warm and comfortable feeling of the occupant and aids in the space heating of the box.

As stated above, the interior of the left wall is mostly covered with a solid sheet of 0.0005 inch thick aluminum foil. The right wall is largely covered with 0.005 inch thick aluminum foil 6¼ inch wide circular strips divided up into 6¼ to ten inch lengths spaced about one inch apart. Part of the right wall is covered by 6¼ inch squares of aluminum foil spaced about one half inch apart. The aluminum foil on the opposite walls provides infrared reflecting surfaces to produce thermodynamic resonance heating. The aluminum foil is also a good conductor of infrared or heat energy. If one places the hand against the solid aluminum foil on the interior of the left wall it feels considerably colder to the touch than the 6¼ inch pieces of aluminum foil on the interior of the right wall. If the wall feels cold it is drawing heat out of the body which detracts from a warm and comfortable feeling. Therefore the aluminum foil on the side walls is broken up into small pieces or segments to provide infrared reflection to product thermodynamic resonance without providing much heat conduction to draw heat out of the body. The thermodynamic resonance heating contributes one or two degrees to the overall space heating of the box.

As stated above, the tungsten filament light bulbs produce electromagnetic waves in the microwave range. The three faces of the CCR act as a three dimensional electromagnetic circuit when excited by the microwave energy from the tungsten light bulb. A series of electromagnetic wave interference patterns or standing waves are set up in front of the CCR aperture from the central axis to the edges of the aperture. Using a sensitive microwave detector one can plot some standing waves that are transverse to the central axis of the CCR. For example, there is a transverse standing wave at about eight inches from the tungsten filament. There is a band of transverse standing waves that appears to be continuous between twenty inches and twenty-five inches from the filament. Other transverse standing waves appear at about thirty-four inches, 39¾ inches and 56¼ inches in front of the filament.

In addition to inverse square law radiation from the bulb, these standing waves conduct heat from the hot bulb along the field lines of the standing waves. Using the hand one can feel a warm beam coming out from the light bulb along the central axis of the CCR for several feet from the bulb and the beam feels especially warm out to about twenty-five inches from the tungsten filament. This warm beam, especially between twenty and twenty-five inches from the filament of the bulb, encompasses the head of the human occupant which gives the occupant the initial warm feeling in the box.

These electromagnetic waves from the tungsten filament bulb strike the ¾ hydrogen cubit (approximately 18.75 inches) radius elements or quarter circles of the CCR, corresponding to the bulb, ceiling, side and back. The ¾ hydrogen cubit radius quarter circles of copper form the radiating elements of a microwave antenna. This microwave energy radiates from the CCR and from the ¾ hydrogen cubit radius radiating elements in a plane to excite the co-planar ¼ hydrogen cubit or quarter wave elements of the copper foil circles surrounding the quarter circle of the corner cube reflector. This captures some of the electromagnetic energy being radiated from the tungsten filament bulb in the form of radio frequency energy and may convert some of the radio frequency energy to heat energy in the copper foil and aluminum foil. While this R.F. excitation of the metal foil in the plane of the radiating elements of the CCR may contribute to the warm feeling of the occupant in the box, tests indicate that any possible R.F. heating of this metal foil is negligible with the relatively low power microwave energy radiating from the tungsten bulb. The warm radiant beam along the central axis of the CCR and the R.F. transverse standing waves between twenty and twenty-five inches from the tungsten filament striking the head of the occupant contribute to the warm feeling of the occupant. The principle contributions to the space heating of the box are the thermodynamic resonance heating, the radiation, the convection and the conduction heating.

As the space heating of the box approaches 70° F. the heating rate begins to decrease. On repeated trials, the enclosure of this example two heated up to ten to twelve degrees above the room temperature outside the box in about twenty minutes. Cool air can be felt coming in the lower half of the two inch wide slit at the front door. Heat is escaping from the top half of the slit in the front door. This provides ventilation for the occupant of the box. In a 60° F. environment outside the box, the occupant can feel warm and comfortable in about a 70° F. enclosure with the expenditure of 155 watts of power for heating and lighting. The large window at the front of the box provides for television viewing and the like.

EXAMPLE 3

The box of example three is a horizontal version of the box/enclosure concept designed for lying down and sleeping rather than sitting up and watching television, reading or working. The interior dimensions are 1½ hydrogen cubits high (about 37 9/16 inches) by 1½ hydrogen cubits wide by three hydrogen cubits long (75 plus inches). Similar to the enclosure of example two, the enclosure of example three is constructed of dimensionally stable material such as plywood or Masonite, lined on the outside with foam plastic insulation board or other appropriate insulation material and lined on the inside with heat reflecting material such as aluminum foil, copper foil, heat reflecting paint or sheet plastic coated with a good infrared reflecting material such as aluminum, silver or gold. The heat reflecting lining material on the interior top of ceiling of the box is thicker than the material on the sides so it is a good conductor of heat as well as a good reflector of heat. The heat reflecting material lining the interior of the box/enclosure must be sturdy enough to withstand the abrasion of a sleeping bag or the like. The rear of the box is enclosed with material similar to the wall material. There are two corner cube reflector (CCR) lights in the upper rear corners of the box. The light bulbs for the CCRs are selected to produce the desired heating for the occupant inside the box, but they are about 60 watts each. Vents are placed in the walls of the box to provide adequate ventilation. The horizontal version of this example three box has not yet been constructed and tested.

Other Uses and Details.

1. One proposed application is to place an enclosure in the room where sitting to read and watch television, work with a computer, etc. The house thermostat, which is normally set at 68° F. to 70° F. is turned down to 60° F. to save money on the heating bill. The occupant sits in the box with the appropriate wattage of lights on, according to the size of the box and the comfort of the occupant. The smaller box/enclosure of example one feels comfortable at about 65° F. to 67° F. and it only consumes 120 watts for heating and lighting. At thirteen cents per kilowatt hour this box can be operated for eight hours for less than thirteen cents.

The larger box/enclosure of example two feels comfortable at about 65° F. but the two light bulbs putting out 155 watts will heat the air in the box to 68° F. to 72° F. At thirteen cents per kilowatt hour, this box can be operated for eight hours for about sixteen cents. Operating this box for eight hours per day for thirty days represents a cost of $4.80.

2. The box/enclosure can be rented out at an airport, railway station, or the like as a temporary office for a person waiting for a plane, train, bus, etc. In this application the box would have telephone jacks for a telephone, fax or internet connection. It would have a small fold down table for a lap top computer, writing desk, etc. It would have electric power outlets for an electric shaver, computer, fax machine, copier, etc.

3. The box/enclosure could be used for a heated and lighted portable toilet or for an outhouse.

4. The box/enclosure concept using thermodynamic resonance, corner cube reflector lights/heaters, infrared reflecting walls, etc. could be used in residential homes for toilet stalls, shower stalls, bathrooms and other rooms in the house. The principle of thermodynamic resonance is not limited to small rooms but works in larger rooms as well.

5. The horizontal version of the box/enclosure (i.e. example three) can be used for a camping tent and would be warmer than a canvas tent. This horizontal version could be used in airports, train stations, etc. for rental as temporary sleeping quarters for passengers between flights.

6. The horizontal version could be used in a Pullman train car, bus, airplane or boat for a berth.

7. Homeless shelters could reduce their heating bills by using the enclosures for sleeping accommodations.

8. The horizontal version could be used for a heated dog house.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A thermally controlled environment maintenance system, comprising in combination:
   a pair of substantially planar parallel side walls with an environment therebetween;
   at least one thermal source between said side walls;
   means to tune a precise distance between said side walls; and
   wherein said tuning means includes a tuning bar located adjacent at least one of said side walls, said tuning bar having at least one adjustable length fastener extending between said tuning bar and said side wall adjacent said tuning bar, said adjustable length fastener adapted to adjust a distance between said tuning bar and said side wall adjacent said tuning bar when said adjustable length fastener is adjusted.

2. The system of claim 1 wherein said adjustable length fastener is coupled to said tuning bar at a center of said tuning bar and said adjustable length fastener is coupled to said side wall adjacent said tuning bar near a vertical centerline of said side wall.

3. The system of claim 2 wherein said adjustable length fastener includes a rotatable bolt and a threaded bore cooperating with a threaded shaft of said bolt.

4. The system of claim 1 wherein said enclosure includes a rear wall extending between a majority of a space between said side walls;
   a roof over said controlled thermal environment, said roof extending between a majority of a space between said side walls; and
   wherein at least two posts extend vertically adjacent forward and rearward edges of at least one of said side walls, said tuning bar having ends thereof affixed to said posts with said tuning bar extending between said posts.

5. The system of claim 1 wherein surfaces of said side walls facing said environment between said side walls have a reflective material thereon such that said surfaces are reflective surfaces, said reflective material reflective of a majority of infrared radiation impacting said reflective material.

6. A thermally controlled environment maintenance system, comprising in combination:
   a pair of substantially planar parallel side walls with an environment therebetween;
   at least one thermal source between said side walls;
   means to tune a precise distance between said side walls;
   wherein surfaces of said side walls facing said environment between said side walls have a reflective material thereon such that said surfaces are reflective surfaces, said reflective material reflective of a majority of infrared radiation impacting said reflective material; and
   wherein said reflective surfaces of said side walls include gaps therein, at least one of said gaps extending a majority of a distance between a front edge and a rear edge of each of said side walls.

* * * * *